United States Patent [19]

Marsoner et al.

[11] Patent Number: 4,912,986
[45] Date of Patent: Apr. 3, 1990

[54] DEVICE FOR THE SELECTIVE CHARGING OF AN ANALYSING APPARATUS

[75] Inventors: Hermann Marsoner, Steinberg; Erich Kleinhappl, Kumberg; Klaus Putz, Kindberg, all of Austria

[73] Assignee: AVL AG, Austria

[21] Appl. No.: 278,922

[22] PCT Filed: Mar. 29, 1988

[86] PCT No.: PCT/AT88/00015
§ 371 Date: Nov. 28, 1988
§ 102(e) Date: Nov. 28, 1988

[87] PCT Pub. No.: WO88/07675
PCT Pub. Date: Oct. 6, 1988

[30] Foreign Application Priority Data

Apr. 3, 1987 [AT] Austria .................................. 828/87

[51] Int. Cl.$^4$ .............................................. G01N 1/00
[52] U.S. Cl. .................................................. 73/864.81
[58] Field of Search .................... 73/863.45, 863.50, 73/864.21–864.25, 864.81, 864.87; 422/64, 68, 81, 83, 88; 204/400, 409

[56] References Cited

U.S. PATENT DOCUMENTS

| | | | |
|---|---|---|---|
| 3,219,416 | 11/1965 | Natelson | 422/64 |
| 3,489,525 | 1/1970 | Natelson | 73/864.81 |
| 3,788,816 | 1/1974 | Rohrbaugh et al. | 422/64 |
| 3,980,093 | 9/1976 | Rhine et al. | 137/1 |
| 4,115,235 | 9/1978 | Capone | 222/225 |
| 4,322,216 | 3/1982 | Lillig et al. | 73/864.25 |
| 4,478,095 | 10/1984 | Bradley et al. | 422/64 |
| 4,750,373 | 6/1988 | Shapiro | 73/864.87 |
| 4,836,038 | 6/1989 | Baldwyn | 73/864.25 |

FOREIGN PATENT DOCUMENTS 0112324 4/1985 European Pat. Off. .

Primary Examiner—Robert R. Raevis
Attorney, Agent, or Firm—Watson, Cole, Grindle and Watson

[57] ABSTRACT

In conventional devices for feeding an analysing apparatus with different media, comprising a feeder unit with fittings for the media to be introduced, the individual media travel different paths between the inlet opening and the measuring chambers, which will result in different conditions of measurement for calibrating media and sample media. The invention eliminates this drawback by providing the feeder unit (1) with feed elements (4, 4') connected with the fittings (5), and by enabling each feed element (4, 4') to be positioned above the sample inlet opening (10) by means of a control unit (8) effecting a translational or rotatory motion of the feeder unit (1), subsequent to which the feed element (4, 4') can be inserted into the sample inlet opening (10) by means of a lifting device acting parallel to the center axis (11) of the sample inlet opening (10).

6 Claims, 4 Drawing Sheets

DEVICE FOR THE SELECTIVE CHARGING OF AN ANALYSING APPARATUS

BACKGROUND OF THE INVENTION

1. Technical Field of the Invention

This invention relates to a device for selectively charging an analysing apparatus with liquid or gaseous sample, reference or cleansing media, comprising a sample inlet opening and a feeder unit with fittings for the media to be introduced.

2. Discussion of the Related Art

Chemical analyses utilizing the kind of test equipment for which the above feeding device is designed, are preferably performed by introducing the sample via the above sample feeding device into the respective measuring chamber, where it is brought into contact with measuring sensors. As a result of the interaction between the sample and these sensors an electric signal will eventually be generated, in general by means of physical or chemical interactions, which is functionally dependent on the concentration of the substance to be determined in the sample.

Devices of this type are known, for instance for carrying out blood gas analyses or electrolyte analyses with the use of electrochemical or optochemical sensors. Examples of the substance concentrations measured include the pH value of a blood sample, the partial pressure of oxygen in molecular solution, the partial pressure of $CO_2$ in molecular solution, and, possibly, a number of ions, enzymes and non-electrolytes contained in the solution, such as glucose, etc.—parameters which in their entirety provide information on the state of the sample and, as such, on the constitution of the test person.

The analysing apparatus should therefore be provided with a device permitting the feeding of all kinds of sample materials into the measuring chambers, and it should also be possible to introduce calibrating liquids, calibrating gases, cleansing solutions, test solutions, i.e. media of a liquid or gaseous type, in a simple manner, with the samples being fed into the inlet opening from their conventional sample containers, such as syringes or capillary glass tubes. Depending on the desired or specified method of operation and optimised sample manipulation, the sample is injected into the inlet opening from a syringe, or it is forced in from capillary tubes of variable length and diameter by means of a pumping device of the analysing apparatus. If gaseous samples or calibrating media are to be introduced, great care should be taken to avoid the build-up of dynamic pressure anywhere in the sample path, since this might falsify the absolute value of the respective partial pressure of the gas.

A device of the above type, for example for feeding selected media into an electrochemical test apparatus, is described in EP-A-O 112 324. This device is provided with a feeder unit carrying fittings for introducing calibrating and reference media, and a sealed piece of pipe positioned in a bore, which is movable relative to the feeder unit. On its end facing away from the measuring chamber this piece of pipe has a fitting for the sample, as well as one or more bores along its circumference, which may be aligned with at least one of the above fittings for the calibrating and reference media by means of a relative motion between the piece of pipe and the feeder unit, which is controlled by a stepping motor.

Although this device has proved successful, it suffers from the drawback that the paths to the measuring chamber travelled by the sample medium and any reference or calibrating media will differ, even if only slightly, where interactions with the materials of the paths and differences in temperature and pressure may occur. This means that sample, reference and calibrating media are not subject to identical conditions, which may result in considerable errors of measurement.

It is an object of the present invention to avoid the disadvantages of previous devices and to propose a feeding device offering identical measuring conditions for all media to be introduced.

SUMMARY OF THE INVENTION

In the present invention this object is achieved by furnishing the feeder unit with feed elements connected with the fittings, and by enabling each feed element to be positioned above the sample inlet opening by means of a control unit effecting a translational or rotatory motion of the feeder unit, subsequent to which the feed element can be inserted into the sample inlet opening by means of a lifting device acting parallel to the center axis of the sample inlet opening. All media to be introduced are thus passed through the same inlet opening by means of the movable feed element, travelling one and the same path between sample inlet opening and the individual measuring chambers within the analysing apparatus. Each of these media has its own feed position on the shiftable or rotatable feeder unit. For sample feeding the feeder unit is moved until the sample inlet opening is freely accessible from outside and may be connected with a sample container, for instance a syringe or a capillary tube.

In order to break the contact between one of the tightly sealing feed elements and the sample inlet opening, and to establish contact with a neighboring feed element, the movable or rotatable feeder unit is lifted in the direction of the center axis of the sample inlet opening, upon which a translational or rotatory motion and, subsequently, another axial motion is effected in order to insert the neighboring feed element.

The question as to whether the feeder unit should be designed for a translational or a rotatory motion in order to properly align feed elements and sample inlet opening is of no consequence for the invention.

A special variant of the invention provides that the feeder unit be configured as a distributor disk which is mounted on a carrier shaft connected to a driving unit and positioned in a housing, whose axis is parallel to the center axis of the sample inlet opening at a distance r, and that the feed elements be located on the distributor disk at a distance r to the axis, preferably in equidistant arrangement. For the sake of simplicity the two modes of motion of the feeder unit will not be mentioned explicitly in the following, since in the preferred variant the device is provided with a feeder unit configured as a distributor disk and the feed elements located on this disk are positioned above the sample inlet opening by a rotatory motion. The axial motion normal to the distributor disk, which is required to establish a sealing contact between the feed elements and the sample inlet opening, is effected by a control unit.

In order to facilitate the mounting of various feed elements the invention provides that the feed elements be placed on docking disks, which are situated in bores of the distributor disk and are replaceable if required, and that the distributor disk have a recess in the sample feed position. Instead of a recess in the distributor disk it would also be possible to leave open one of the bores by omitting the respective docking disk, and to establish contact between the respective sample container and the sample inlet opening via this opening.

As each of the feed positions on the rotatable distributor disk must be determined within certain tolerances and controlled by a position monitoring device, a further development of the invention provides that a position sensing device be added, whose movable part, which is preferably configured as a disk, is connected to the carrier shaft, and whose stationary part is attached to the housing. Position sensing may be effected by electromechanical or opto-electric means in a conventional manner.

An enhanced version of the invention provides that the lifting device be configured as a lifting gate whose position is concentric to the carrier shaft, which gate cooperates with the driving unit—the distributor disk, which is initially prevented from rotating by a braking device, being lifted against the force of a spring by a pulling element fastened on the carrier shaft, and further, that—as soon as the pulling element is resting against a stop of the lifting gate—the distributor disk should start rotating through the number of positions given by the control unit. In this simple manner the rotatory motion imparted by the driving unit is transformed into the lifting/turning motion required for the distributor disk, the invention providing that the braking device be constituted by a jacket tube enveloping the carrier shaft concentrically, which tube is supported in the housing and has one or more axial guiding grooves receiving the pulling element, and cooperates with one or more spring-loaded braking shoes arranged radially in the housing. Preferably, two braking shoes are used, which are placed radially opposite of each other, thus compensating the moments exerted by the braking device upon the jacket tube.

According to the invention the lifting device may also be configured as a lifting magnet, preferably located in the housing, or as a motor with a helical spindle. The lifting motion may also be effected by a pneumatic or hydraulic lifting device.

Finally, another variant of the invention provides that the fittings connecting to the feed elements, which are preferably configured as tubes or hoses, should run radially along the distributor disk, and then parallel to the axis of the carrier shaft. In the area of the carrier shaft connecting elements may be provided, where the tubular fittings are joined to hoses leading to the storage containers.

BRIEF DESCRIPTION OF THE DRAWINGS

Following is a more detailed description of the invention as illustrated by the accompanying drawings, in which FIGS. 1 and 2 give partially schematic views from above and the side of a device as described by the invention, FIG. 3 gives a sectional view of a variant of the invention cut along line III—III in FIG. 4, FIG. 4 a section along line IV—IV in FIG. 3, FIG. 5 a detail of the variant in FIGS. 3 and 4, and FIG. 6 another variant of the invention, the section corresponding to that of FIG. 3.

DETAILED DESCRIPTION OF THE PREFERRED EMBODIMENTS

Figure 1:
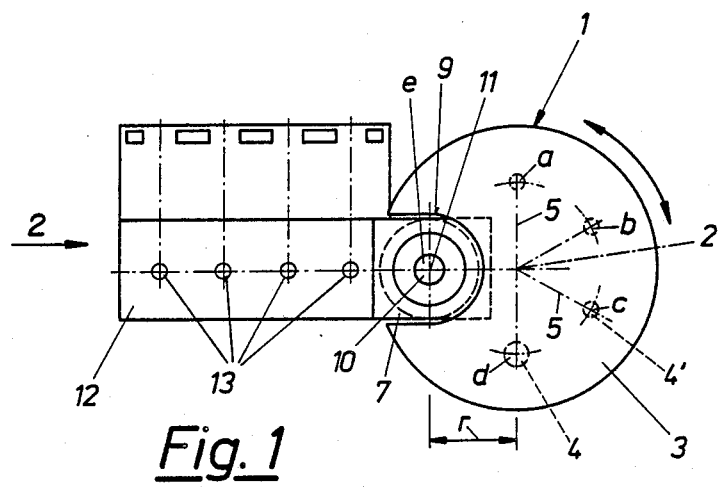
Figure 2:
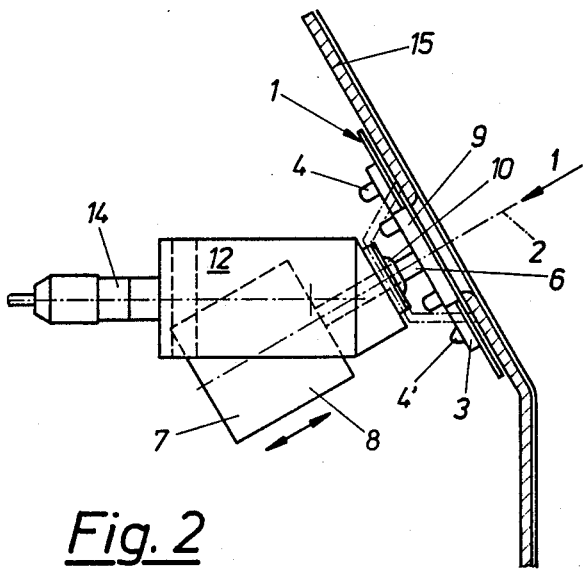

In the schematical views of the device presented in FIGS. 1 and 2 a movable feeder unit 1, which is configured as a distributor disk 3 rotatable about the axis 2, has several feed elements 4, 4' located at a distance r from the axis 2 in feed positions a to d, which elements are connected via fittings 5 with the media to be introduced from containers not shown here. The distributor disk 3 is supported on a carrier shaft 6 in a housing 7 containing, among others, the control unit 8 for the geometric shifting of the distributor disk 3. In the feed position e the distributor disk 3 has a recess 9, such that in this position the sample inlet opening 10 is ready to receive the sample, which is entered by a pipette, syringe or other containers that are inserted into the inlet opening 10.

The sample inlet opening 10, whose center axis 11 is parallel to the axis 2 of the carrier shaft 6 at a distance r, is directly connected to the measuring chamber 12 (not presented in detail here), which latter contains sensors 13 and corresponding measuring electrodes 14. The feed elements 4, 4' situated on the distributor disk 3 in positions a to d, can be aligned with the center of the sample inlet opening by a rotatory and axial motion relative to the sample inlet opening 10, such that the feed elements 4, 4' configured as specifically designed cylindrical or conical pieces of a tube-like character can be brought into sealing contact with the sample inlet opening 10. Number 15 refers to a cover or front plate not shown in FIG. 1.

Figure 3:
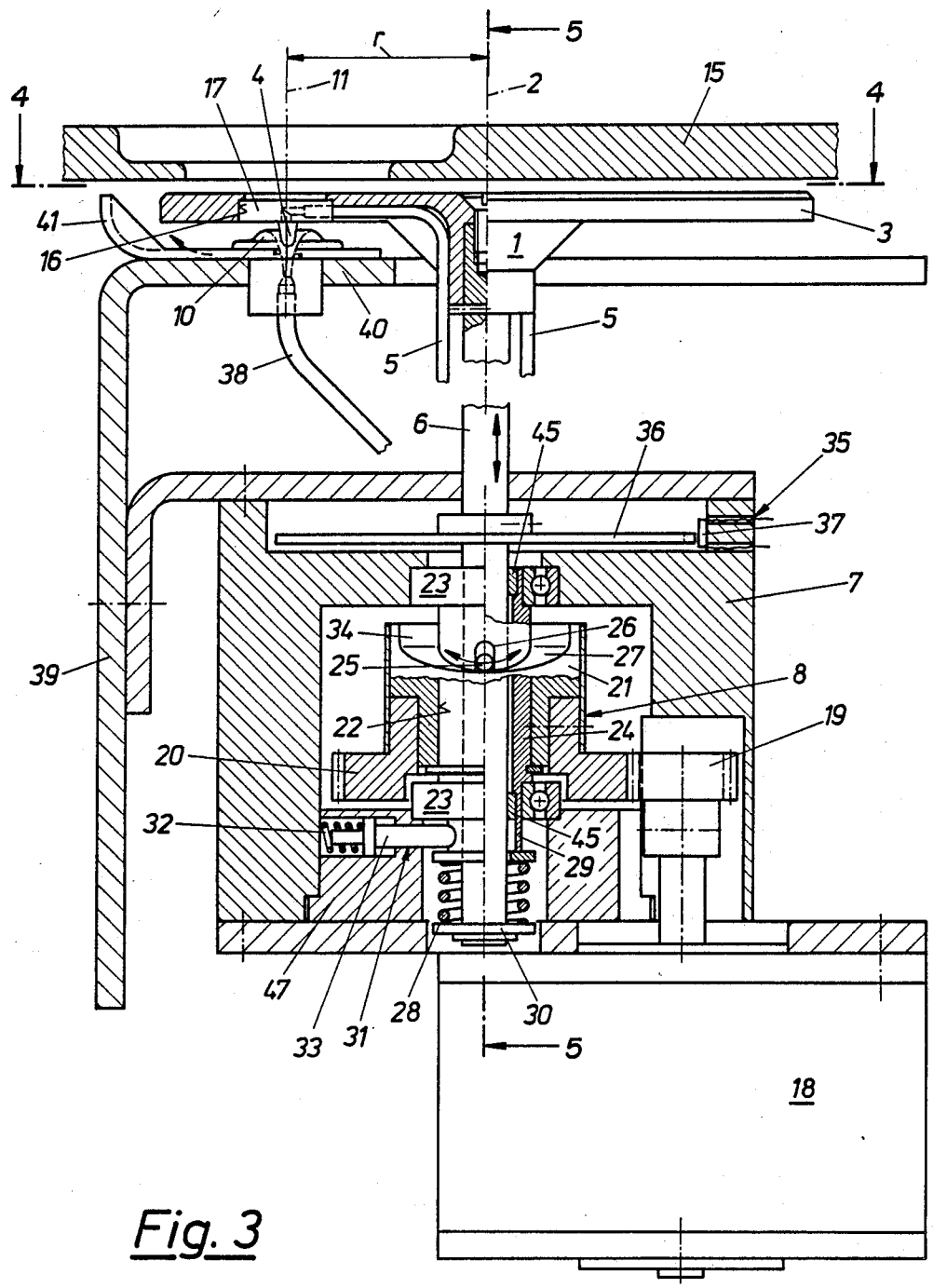
Figure 4:
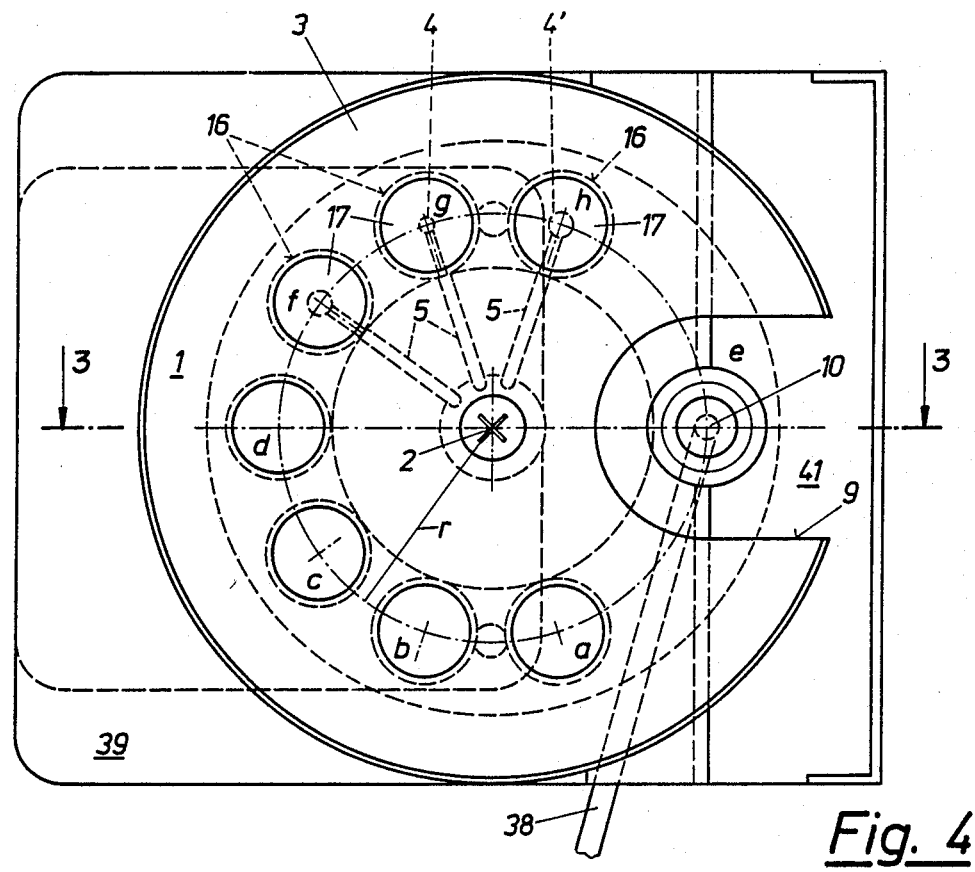

FIGS. 3 and 4 give a more detailed view of a preferred variant of the feeding device described by the invention for an analysing apparatus. The feeder unit 1 designed as a distributor disk 3 has positions a to h, all of which—with the exception of position e—have bores 16, in which are located docking disks 17 receiving the feed elements 4, 4' connected with the fittings 5. A control unit 8 to be described in more detail, comprising the driving gear and control elements (not shown here) of the driving motor 18, transforms the rotatory motion of the motor into a lifting/turning motion of the carrier shaft 6 and thus the distributor disk 3. During this process the motor 18 cooperates via a gear 19 with the rim gear 20 of a lifting device located concentrically to the carrier shaft 6 and comprising a lifting gate 21. In an axial bore 22 of the lifting gate 21 a jacket tube 24 is placed, which is rotatably mounted in the housing 7 by means of two bearings 23, and envelopes the carrier shaft 6, the latter being provided with a pulling pin 25 extending radially outwards, which is guided in an axial groove 26 of the jacket tube 24, such that the carrier shaft 6 can only perform a limited axial shift in the tube 24. The pulling pin 25 extending beyond the guiding groove 26 rests against a guiding face 27 of the lifting gate 21 presenting an upward slope in a circumferential direction, and is pressed against the guiding face 27 by the force of a spring 28 resting against the end 29 of the jacket tube 24 on one side and against a stop 30 of the carrier shaft 6 on the other side. A braking device 31 acting on the jacket tube 24, which is located in the housing 7 and consists of a radially active braking shoe 33 loaded by a spring 32, will prevent the jacket tube 24 from turning together with the feeder unit 1 during its lifting motion; after the pulling pin 25 has come to rest against a stop 34 of the lifting gate 21, the braking force is overcome and rotatory motion sets in.

The control unit 8 also comprises a position sensing device 35 provided with a disk 36, which disk is mounted on the carrier shaft 6 and has markings, and which cooperates with a stationary part 37 connected to the housing 7, part 37 preferably being furnished with electro-mechanical or opto-electronic means of position sensing.

Switching the sample feeding device from one feed position to the next is as follows. When the lifting gate 21 is set into motion by the motor 18 the pulling pin 25 starts gliding on the sloping guiding face 27 of the lifting gate 21, and the carrier shaft 6 is lifted in a given direction against the force of the spring 28 without any rotating movement of the distributor disk 3. At this stage the carrier shaft 6 is still prevented from rotating by the braking device acting upon the jacket tube 24. In the given variant the force of the spring is surmounted as the distributor disk is pushed away from the sample inlet opening 10, thus it is the force of the spring that provides the pressure with which the individual docking disks 17, together with the feed elements 4, 4', are pressed against the inlet opening 10.

Once the lift resulting from the sloping face of the gate has been carried out by an axial movement of the carrier shaft 6, the pulling pin 25 rests against the stop 34 of the lifting gate 21, thereby surmounting the braking force of the braking device 31, which will enable the distributor disk 3 to start rotating through the desired number of positions, as controlled by the position sensing device 35. The distributor disk 3 will come to a standstill as soon as it has reached this position, which may correspond to a certain function, for example, if air from outside is to be blown through the sample inlet opening 10 for the purpose of drying the sample paths.

As a rule, however, the direction of the motor 18 is reversed, and the pulling pin 25 moves away from the stop 34, thus inducing the axial return motion of the carrier shaft 6 and a lowering of the feed elements 4, 4' of the distributor disk 3 onto the sample inlet opening 10.

Number 38 refers to the sample path, preferably a metal tube, representing the shortest connection between the sample inlet opening 10 and the measuring chambers not shown here.

In a preferred version the tubular fittings 5 are guided along the carrier shaft 6 concentrically to its axis 2, where they may be inserted into a closely fitting connecting element (not shown here), leading via a connecting tube to the storage containers holding the respective liquid or gaseous media.

The housing 7 is mounted in a frame 39, into whose part 40 the sample inlet opening 10 is inserted, which is configured as a flexible funnel. The inlet opening 10 is surrounded by a removable, easy-to-clean drip tray 41. Whereas in FIG. 3 a docking disk 17 is positioned above the inlet opening 10, the distributor disk 3 is turned by 72 degrees in FIG. 4, thus positioning the recess 9 above the inlet opening 10. In FIG. 4 the fittings 5 and the feed elements 4, 4' are indicated only for the feed positions f, g, h.

Figure 5:
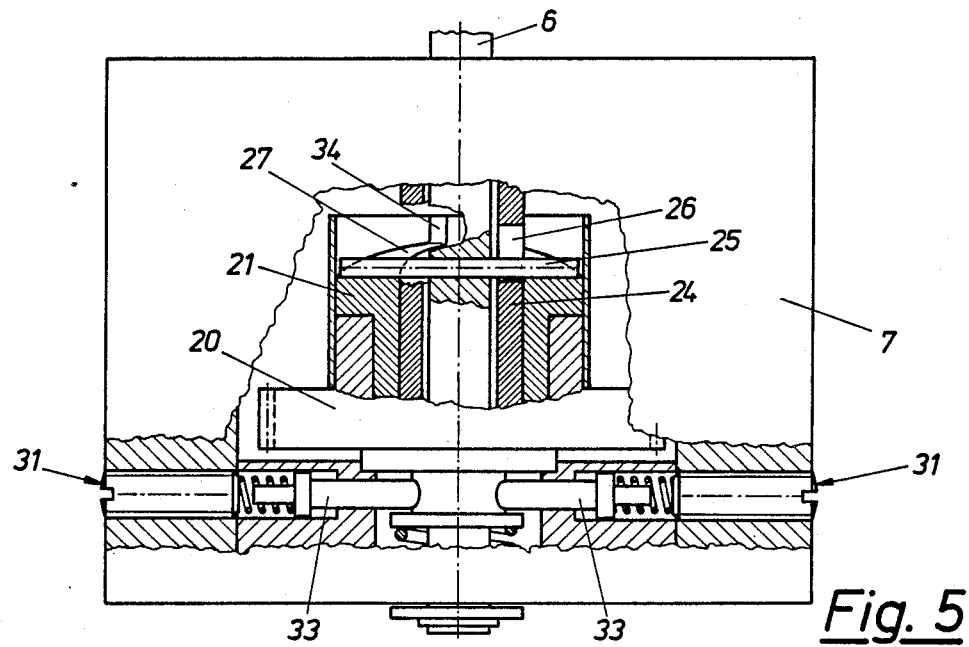

In FIG. 5 the lifting gate 21 and the pulling pin 25 cooperating with it are presented as sectional views corresponding to that in FIG. 3. Unlike in FIG. 3, two braking units 31 have been included here.

Figure 6:
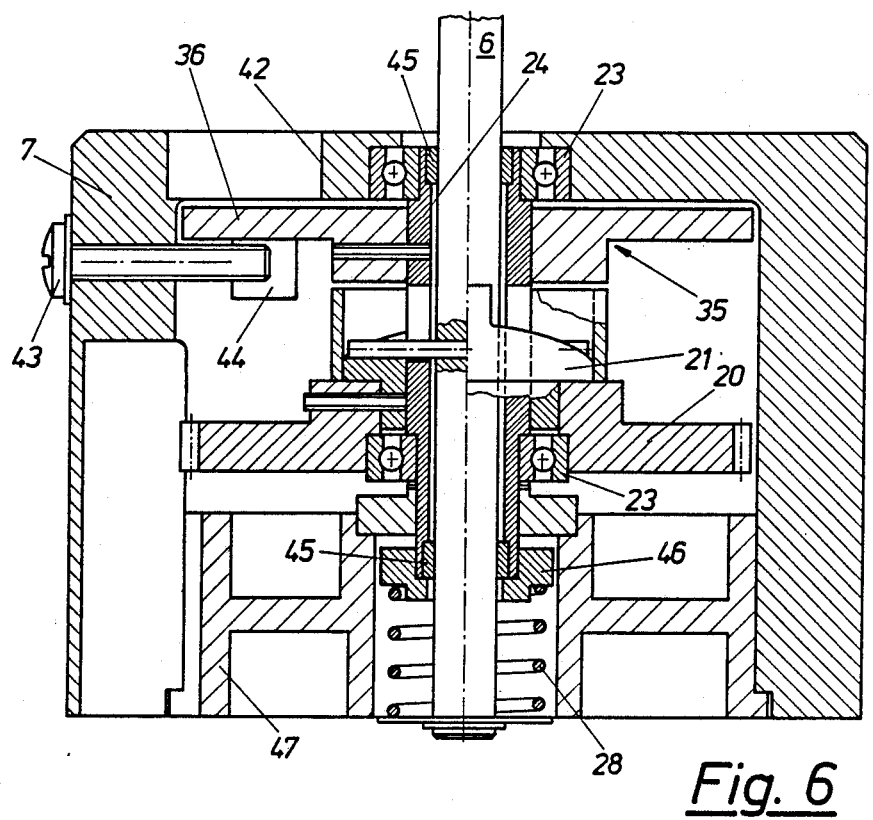

FIG. 6 shows a further variant, in which the distributor disk and the feeder funnel have again been omitted (cf. FIG. 5). In this variant the disk 36 of the position sensing device 35 is within the housing 7. The stationary part belonging to it can be inserted into bore 42 of the housing 7; the stop 44 on the disk 36 cooperating with a screw 43 will limit the angle of rotation of the carrier shaft 6 to approximately 350 degrees, thereby preventing damage of the connecting tubes (not shown here) departing from the fittings 5.

The carrier shaft 6 is held in the jacket tube 24 by two plain bearings 45. The braking device not shown here cooperates with a braking shoe 46 located on the end 29 of the jacket tube. The housing 7 is sealed by a cover 47.

We claim:

1. A device for selectively charging an analyzing apparatus with a fluid sample medium, and at least one reference medium and one cleansing medium, comprising a sample inlet opening and a feeder unit with fittings for said reference and cleansing media to be introduced, wherein said feeder unit is configured as a distributor disk, which is mounted on a carrier shaft connected to a driving unit, the axis of said shaft is parallel to the center axis of said sample inlet opening at a distance r, at which distance r feed elements are located on said distributor disk, said feed elements being connected with said fittings, and wherein each of said feed elements is positionable above said sample inlet opening by a control unit effecting a rotatory motion of said feeder unit, so that said feed element positioned above said sample inlet opening is insertable into said sample inlet opening by means of a lifting device acting parallel to said center axis of said sample inlet opening, and wherein said distributor disk has a recess in a sample feed position.

2. A device according to claim 1, wherein the feed elements are placed on docking disks, which are situated in bores of the distributor disk and which are replaceable if required.

3. A device according to claim 1, further comprising a position sensing device with a disk-shaped movable part which is connected to said carrier shaft, and a stationary part which is attached to a housing which surrounds said position-sensing device.

4. A device according to claim 1, wherein said lifting device is configured as a lifting gate whose position is concentric to said carrier shaft and which cooperates with said driving unit, wherein said distributor disk, which is initially prevented from rotating by a braking device, is lifted against the force of a spring by a pulling element fastened on said carrier shaft, and wherein, as soon as said pulling element is resting against a stop of said lifting gate, said distributor disk starts rotating through a number of positions given by said control unit.

5. A device according to claim 4, wherein said braking device is constituted by a jacket tube enveloping said carrier shaft concentrically, wherein said tube is supported in the housing, and has at least one axial guiding groove receiving said pulling element, and cooperates with at least one spring-loaded braking shoe arranged radially in the housing.

6. A device according to claim 1 wherein said fittings connecting to said feed elements, run radially along said distributor disk, and then parallel to the axis of said carrier shaft.

* * * * *

UNITED STATES PATENT AND TRADEMARK OFFICE
CERTIFICATE OF CORRECTION

PATENT NO. : 4,912,986
DATED : April 3, 1990
INVENTOR(S) : Hermann MARSONER et al.

It is certified that error appears in the above-identified patent and that said Letters Patent is hereby corrected as shown below:

On the title page, Column 1, item (73), change "Austria" to read --Switzerland--.

Signed and Sealed this

Fifteenth Day of January, 1991

*Attest:*

HARRY F. MANBECK, JR.

*Attesting Officer*   *Commissioner of Patents and Trademarks*

UNITED STATES PATENT AND TRADEMARK OFFICE
CERTIFICATE OF CORRECTION

PATENT NO. : 4,912,986
DATED : April 3, 1990
INVENTOR(S) : HERMANN MARSONER ET AL.

It is certified that error appears in the above-identified patent and that said Letters Patent is hereby corrected as shown below:

On the title page, column 1, item (73), change "Austria" to read --Schaffhausen, Switzerland--.

This certificate supersedes Certificate of Correction issued January 15, 1991.

Signed and Sealed this

Tenth Day of December, 1991

Attest:

HARRY F. MANBECK, JR.

*Attesting Officer*    *Commissioner of Patents and Trademarks*